(12) United States Patent
Kim

(10) Patent No.: US 6,542,236 B1
(45) Date of Patent: Apr. 1, 2003

(54) ILLUMINATING AND OPTICAL APPARATUS FOR INSPECTING SOLDERING OF PRINTED CIRCUIT BOARD

(75) Inventor: Jae Seon Kim, Yongin (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 09/763,717

(22) PCT Filed: Aug. 27, 1999

(86) PCT No.: PCT/KR99/00490

§ 371 (c)(1),
(2), (4) Date: Mar. 22, 2001

(87) PCT Pub. No.: WO00/13005

PCT Pub. Date: Mar. 9, 2000

(30) Foreign Application Priority Data

Aug. 27, 1998 (KR) .............................................. 98/34949
Jul. 27, 1999 (KR) .............................................. 99/30511

(51) Int. Cl.⁷ .............................................. G01B 11/24
(52) U.S. Cl. .................... 356/394; 356/237.1; 348/126; 250/559.34
(58) Field of Search ........................... 356/237.1, 237.2, 356/237.3, 237.4, 237.5, 394, 613; 250/559.08, 559.34, 559.2; 348/125, 126

(56) References Cited

U.S. PATENT DOCUMENTS

| | | | | |
|---|---|---|---|---|
| 4,677,473 A | * | 6/1987 | Okamoto et al. ............... | 382/8 |
| 4,988,202 A | * | 1/1991 | Nayar et al. ................. | 356/394 |
| 5,032,735 A | * | 7/1991 | Kobayashi et al. .......... | 356/394 |
| 5,039,868 A | * | 8/1991 | Kobayashi et al. .......... | 250/572 |
| 5,064,291 A | * | 11/1991 | Reiser ........................ | 356/394 |
| 5,072,127 A | * | 12/1991 | Cochran et al. ............. | 356/240 |
| 5,166,985 A | * | 11/1992 | Takagi et al. ................ | 382/8 |
| 5,245,671 A | * | 9/1993 | Kobayashi et al. ............ | 382/8 |
| 5,267,217 A | * | 11/1993 | Tokura et al. ............... | 356/237 |
| 5,455,870 A | * | 10/1995 | Sepai et al. ................. | 382/147 |
| 5,519,496 A | * | 5/1996 | Borgert et al. ............... | 356/394 |
| 5,686,994 A | * | 11/1997 | Tokura ........................ | 356/394 |
| 6,070,986 A | * | 6/2000 | Yoneda ....................... | 362/33 |
| 6,122,048 A | * | 9/2000 | Cochran et al. ........... | 356/239.4 |
| 6,166,393 A | * | 12/2000 | Paul et al. ............... | 250/559.08 |

FOREIGN PATENT DOCUMENTS

| | | | |
|---|---|---|---|
| JP | 07-27531 | * | 1/1995 |
| JP | 08-128963 | * | 5/1996 |
| JP | 10-90191 | * | 4/1998 |
| JP | 10-160426 | * | 6/1998 |

* cited by examiner

Primary Examiner—Hoa Q. Pham
(74) Attorney, Agent, or Firm—Staas & Halsey LLP

(57) ABSTRACT

An illuminating and optical apparatus for inspecting soldering of an inspecting part on a PCB includes an illuminating and optical apparatus collecting light emitted by first and second illuminating units. The first and second illuminating units each includes lamps arranged in rows around a view axis of large and small view cameras at a predetermined angle, wherein the large and small view cameras draw sufficient light reflected by the inspecting part and obtain different view sizes of images in accordance with the sizes of the inspecting part. An illuminating and optical apparatus collects light emitted by the first and second illuminating units.

32 Claims, 8 Drawing Sheets

☐ BRIGHT AREA
■ DARK AREA

☐ BRIGHT AREA
■ DARK AREA

ILLUMINATING AND OPTICAL APPARATUS FOR INSPECTING SOLDERING OF PRINTED CIRCUIT BOARD

TECHNICAL FIELD

The present invention relates to an illuminating and optical apparatus for inspecting soldering of a printed circuit board, and more particularly, to the illuminating and optical apparatus which uniformly illuminates and photographs a variety of electronic parts mounted and soldered on the printed circuit board of a surface mounting apparatus to automatically inspect the mounted and soldered states thereof.

BACKGROUND ART

In general, a surface mounting apparatus is used for automatically fixing a variety of electronic parts, such as an integration element, a resistor, a condenser, and the like by directly soldering the electronic parts on the printed circuit board (hereinafter referred to as PCB). That is, without separate soldering lead wires to fix on the PCB, those electronic parts have electrodes for directly soldering the electrodes. In this way, there will be advantages such as reducing the size of electronic parts, substantially improving assembling and manufacturing speed because a separate hole does not have to be formed for fixing electronic parts on the PCB, and decreasing the size of a product.

In soldering various parts with the surface mounting apparatus, the parts are so small that they can not be accurately mounted on the PCB or the amount of solder is so great that the potential may be high for two adjacent electrodes bringing about a lot of errors, such as a short circuit and the like. Therefore, after finishing up soldering parts, mounted and soldered states thereof are inspected to decrease a defective rate of products.

In order to inspect the mounted and soldered states of the parts soldered at the surface mounting apparatus, a number of workers are needed for manual inspection, but it is hard to achieve uniformity of the manual inspection.

Therefore, in case of inspecting the mounted and soldered state of the part soldered on the PCB, an automatic inspection process has been performed by illuminating, and photographing the inspecting parts with a camera and screening the mounted and soldered states of the parts with resultant photographs.

FIG. 1 is a schematic view illustrating an embodiment of a structure and an operational state of a conventional illuminating and optical apparatus which illuminates and photographs mounted and soldered states of an electronic part on a PCB for automatic inspection.

At this time, reference numeral 10 denotes the PCB. Reference numeral 11 denotes an electronic part such as integration element, resistor and condenser and the like of which mounted and soldered states on the printed circuit board are inspected. Also, reference numeral 12 denotes a disturbing part adjacently positioned to the inspecting part soldered on the PCB, which interferes with the proceeding route of the light in inspecting the mounted and soldered states of the part on the PCB.

Reference numerals 13, 14, and 15 respectively denote upper, middle and lower light emitting parts, all of which illuminate the inspecting part 11. All of those light emitting parts are made up of a plurality of lamps arranged in a ring shaped fixtures of different diameters and different heights therebetween.

Symbols H1, H2, and H3, respectively, denote a height of the upper, middle, and lower light emitting parts 13, 14, 15 arranged at different heights having the relationship of H1>H2>H3. On the other hand, symbols D1, D2, and D3, respectively, denote a diameter of the upper, middle, and lower light emitting parts 13, 14, 15 arranged at different diameters having the relationship of D1<D2<D3.

All of those light emitting parts 13, 14, 15 are fixed with an identical center axis.

At this time, for instance, light emitting diodes are used for a plurality of lamps.

Reference numerals 16, 17, respectively, denote a camera and lenses positioned over the center axis of all the upper, middle, and lower emitting parts 13, 14, 15 for photographing the inspecting part 11 while being illuminated by the upper, middle, and lower light emitting parts 13, 14, 15.

For example, the camera 16 takes a photograph of the inspecting part 11 with a charged coupled device CCD.

When the conventional illuminating and optical apparatus thus constructed is used for inspecting the mounted and soldered states of the part 11 on the PCB 10, all the lamps of the upper, middle, and lower light emitting parts 13, 14, 15 are turned on to illuminate the inspecting part 11.

At this state, the camera 16 takes an image of the inspecting part 11 illuminated by the upper, middle, and lower light emitting parts 13, 14, 15 through the lenses 17. The photographed image of the inspecting part 10 is inputted and further processed by an inspection apparatus, such as an inspection computer system or the like to inspect the mounted and soldered states of the part 11 on the PCB 10.

However, in the conventional illuminating and optical apparatus, the incident light of the upper, middle, and lower light emitting parts 13, 14, 15 is focused only on a position of the inspecting part 11, that is, at a center of a photographing view of the camera 16. As a result, the center of the photographed image is brightest. On the other hand, the closer a position gets to the edge of the image, the image becomes darker.

Therefore, as an image processing condition should be differently set up depending on positions of the same image of an identical inspecting part 11, it is difficult to make a standard inspection condition.

FIG. 2 is a schematic view illustrating another embodiment of a structure and an operational state of a conventional illuminating and optical apparatus. As shown in FIG. 2, the illuminating and optical apparatus includes light diffusers 13a, 14a, 15a below the upper, middle, and lower light emitting parts 13, 14, 15.

In this case, light illuminated by the upper, middle, and lower light emitting parts 13, 14, 15 are diffused by the light diffusers 13a, 14a, 15a, thereby relatively evenly illuminating the inspecting part 11.

However, as the illuminating light is diffused, the amount of light actually directed on the inspecting part 11 has substantially decreased. Therefore, it is difficult to adequately illuminate the inspecting part 11 for inspection. In addition, because the diffusion degree of light varies in response to the quality of a material of the diffuser, it is difficult to evenly illuminate the inspecting part 11 for inspection up to the required level.

Besides the aforementioned problems, there are further problems, which will be de scribed below, in the conventional apparatuses for accurately inspecting the mounted and soldered states of the inspecting part 11.

First, as only the upper, middle, and lower light emitting parts 13, 14, 15 are used for illuminating and photographing the inspecting part 11, it has been difficult to distinguish a soldering portion of the inspecting part 11 from a pattern of the PCB 10 or the body of the inspecting part 11, or the electrode of the inspecting part 11 from the body of the inspecting part 11 or the soldering portion. Therefore, it is difficult to simultaneously inspect both, the mounted and soldered states of the inspecting part Second, if the disturbing matter 12 positioned around the inspecting part 11 is larger than the inspecting part 11 itself, the light emitted by the lower light emitting part 15 tends to be interfered with or blocked by the disturbing matter 12, causing a light interference phenomenon. Therefore, the required illumination effect can not be obtained, thereby reducing reliability of the inspection process.

Third, there is no control means available for controlling the brightness of the upper, middle, and lower light emitting parts 13, 14, 15, thereby causing inconveniences when in use.

Fourth, a single size of the camera view is available for grasping the inspecting state. In other words, only the camera 16 is utilized at an identical magnitude for photographing the inspecting part 11. Therefore, it is impossible to adequately correspond to different sizes of the inspecting part 11, thereby reducing the inspecting speed.

SUMMARY OF THE INVENTION

It is an object of the present invention to provide an illuminating and optical apparatus for inspecting soldering of an inspecting part on PCB, including light emitting parts to evenly illuminate the inspecting part; and a camera set comprising different view magnitudes to photograph different view sizes of images in accordance with the sizes of the inspecting part to inspect the mounted and soldered states of the inspecting part.

In order to accomplish the aforementioned object, an illuminating and optical apparatus for inspecting soldering of a PCB, including: a fixed member comprising a horizontal plane at an upper plane thereof and a tilted plane at the side thereof; first illuminating means disposed at the upper plane of the fixed member for illuminating an inspecting part attached to the PCB; second illuminating means disposed at the tilted plane of the fixed member for illuminating the inspecting part to obtain an image having a shade inverted to that obtained by the first illuminating means; control means for controlling a brightness of the first and second illuminating means and turning power thereof on/off; and optical means disposed at the upper plane of the fixed member for photographing large and small views of the inspecting part illuminated by the first and second illuminating means under the control of the control means.

A photograph hole formed on the fixed member, wherein the first illuminating means comprises lamps arranged in ring-shaped fixtures of different diameters therebetween and having identical heights thereto, and the lamps are installed adjacent to the photograph hole of the optical means formed on the fixed member. The second illuminating means comprises lamps arranged in ring-shaped fixtures of different diameters and heights therebetween. The lamps arranged in ring-shaped fixtures located at a lowest end of the second illuminating means are disposed adjacent to a lower portion of the tilted plane of the fixed member. Lamps are arranged in ring-shaped fixtures located at an uppermost portion of the second illuminating means and located at a predetermined angle between a straight line formed by the ring-shaped fixtures arranged at an outermost portion of the first illuminating means connecting a center of the inspecting part positioned at a predetermined height and another straight line formed by the ring-shaped fixtures arranged at the uppermost portion of the second illuminating means connecting the center of the inspecting part positioned at the predetermined height.

Furthermore, the control means includes a power switch; a light control unit varying a resistance value by controlling a plurality of light switches; and an output unit outputting electric current in accordance with the resistance value of the light control unit when the power switch is turned on and applying the electric current to the first and second illuminating means.

The optical means includes reflected light transmitting means for transmitting a half of the light reflected by the inspecting part; large and small view cameras which respectively photograph the half of the light reflected by the inspecting part; and large and small view lenses respectively assembled in front of the large and small view cameras controlling view sizes of images to be photographed by the large and small view cameras. The reflected light transmitting means includes a half mirror of a triangular prism, which enables a half of the light reflected by the inspecting part to transmit to a proceeding direction and the other half of the light to further reflect to an angle of 90 degree. A large view total reflection mirror of a planar mirror to reflect the light reflected by the half mirror at the angle of 90 degrees to identically proceed to the axis of the large view camera [the latter half of the light reflected by the half mirror at the angle of 90 degrees] and the large view lens. A first total reflection mirror including a small view of the triangular prism to change a proceeding direction of the light transmitted through the half mirror at the angle of 90 degrees; and a second total reflection mirror including a small view to reflect again the light of which proceeding direction was changed at 90 degrees by the first total reflection mirror, and to identically advance the light to the axis of the small view camera and the small view lens. Large and small view lenses drawing the light reflected by the total reflection mirror having the large view and the second total reflection mirror having the small view into the large and small view cameras.

DESCRIPTION OF THE PREFERRED EMBODIMENTS

An illuminating and optical apparatus for inspecting a soldered state on the PCB in accordance with the present invention will be described in detail with reference to the accompanying drawings, FIGS. 3 through 9.

Figure 1:
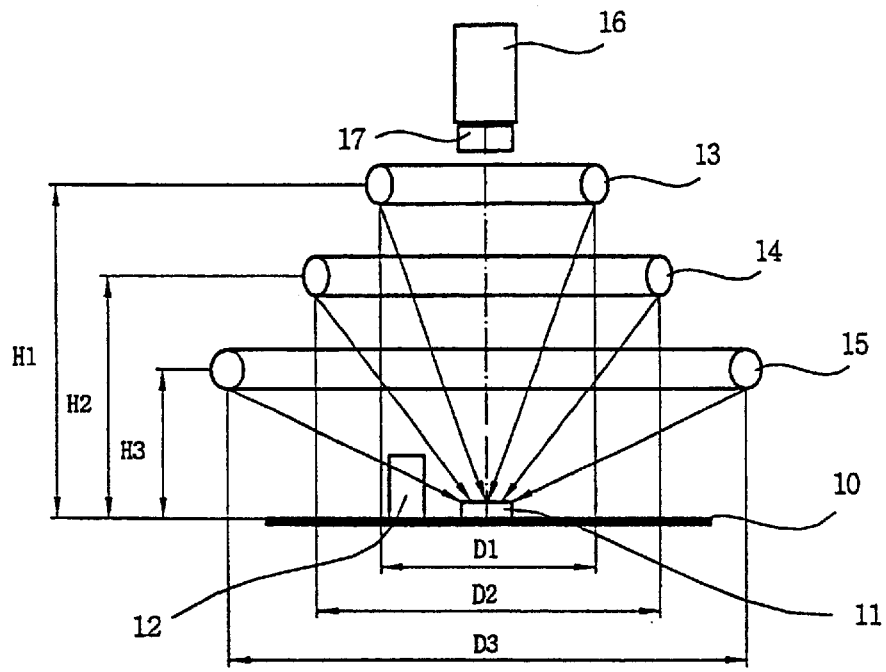
FIG. 1 is a schematic view illustrating an embodiment of a structure and an operational state of a conventional illuminating and optical apparatus.
Figure 2:
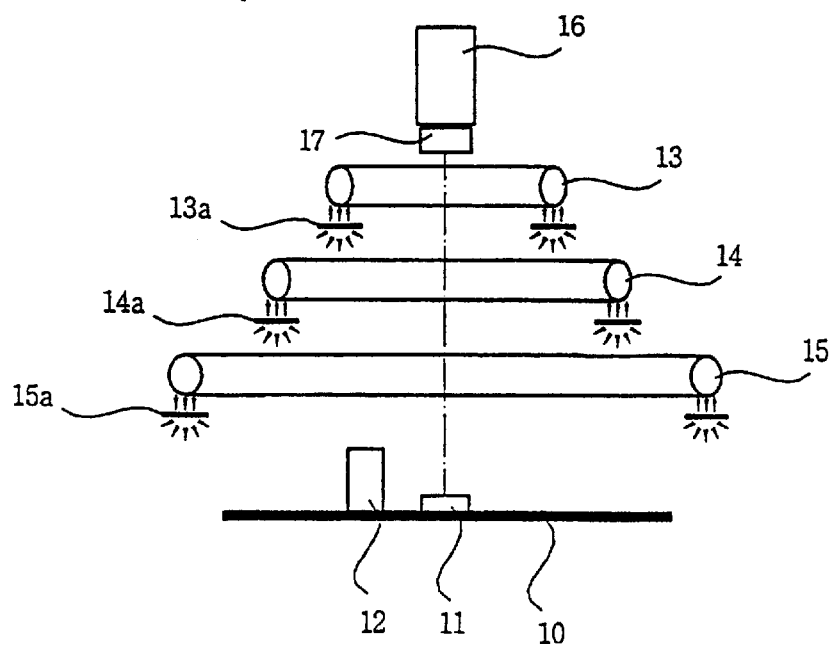
FIG. 2 is a schematic view illustrating another embodiment of a structure and an operational state of a conventional illuminating and optical apparatus.
Figure 3:
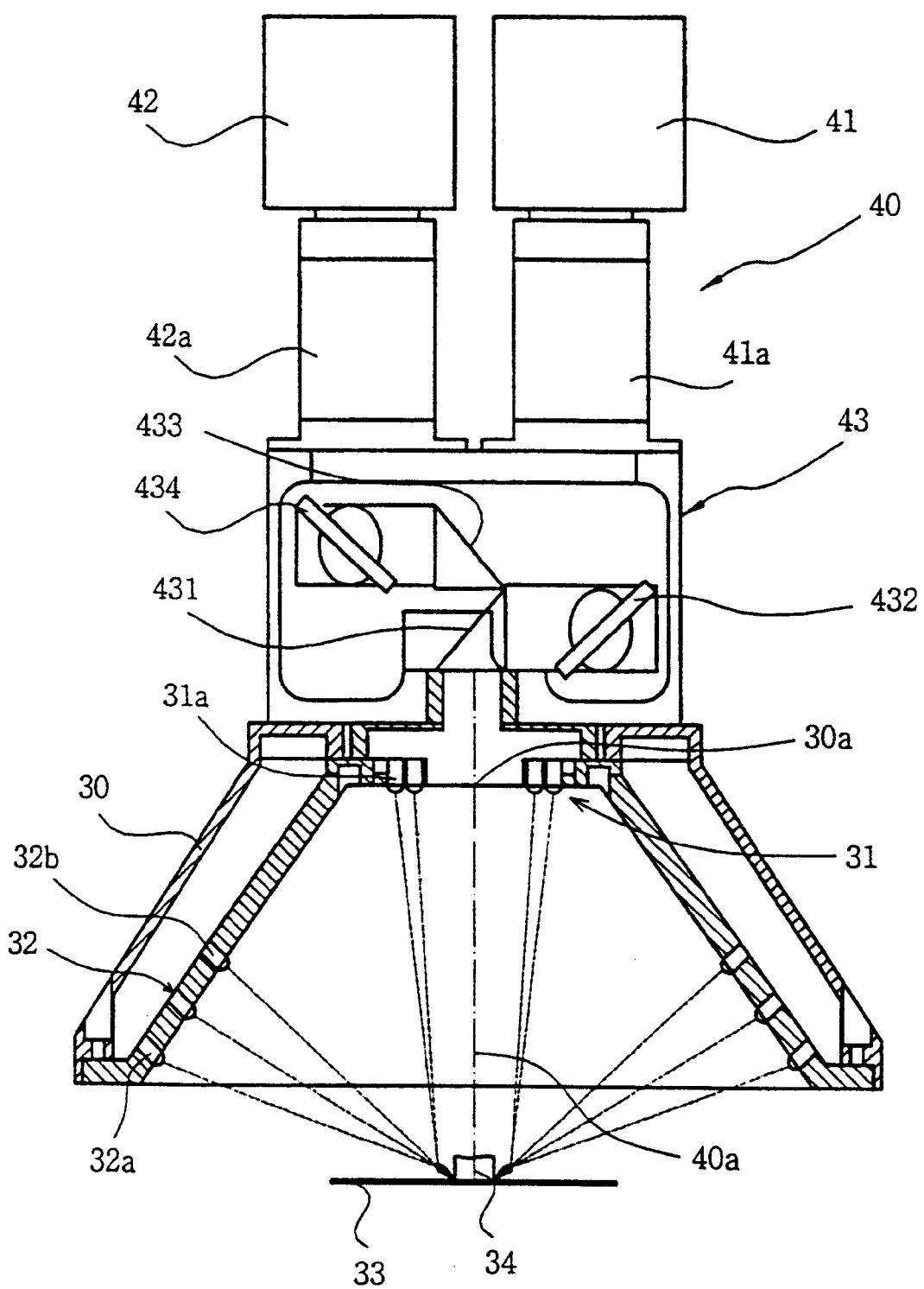
FIG. 3 is a cross-sectional view illustrating a structure of an illuminating and optical apparatus, in accordance with the present invention.

FIG. 3 is a cross-sectional view illustrating a structure and an operational state of an illuminating and optical apparatus of the present invention. At this time, reference numeral 30 denotes a fixed member having an upper plane formed in a horizontal plane and a lateral plane formed in a tilted plane having an approximately circular cone.

First illuminating means 31 is assembled at a horizontally leveled position inside the upper plane of the fixed member 30 and second illuminating means 32 at an inner circumference of a position where the circular cone is formed.

At the center of the upper plane of the fixed member 30, a photograph hole 30a is formed to enable optical means 40 to photograph an inspecting part 34 fixed on a PCB 33, the first illuminating means 31 is disposed at the external side of the photograph hole 30a, and second illuminating means 32 is disposed at the internal side of the tilted plane which forms the circular cone of the fixed member 30. The first and the second illuminating means 31, 32 are selectively turned on/off by control means, which will be described below, to illuminate the inspecting part 34 and to control the brightness of the illuminating light.

The first illuminating means 31 includes a plurality of lamps 31a formed in concentric circles on the same planar level and arranged in a plurality of ring-shaped fixtures having different diameters, for example, two rows of ring-shaped fixtures, are installed close to or adjacent to the external side of the photograph hole 30a.

Figure 4:
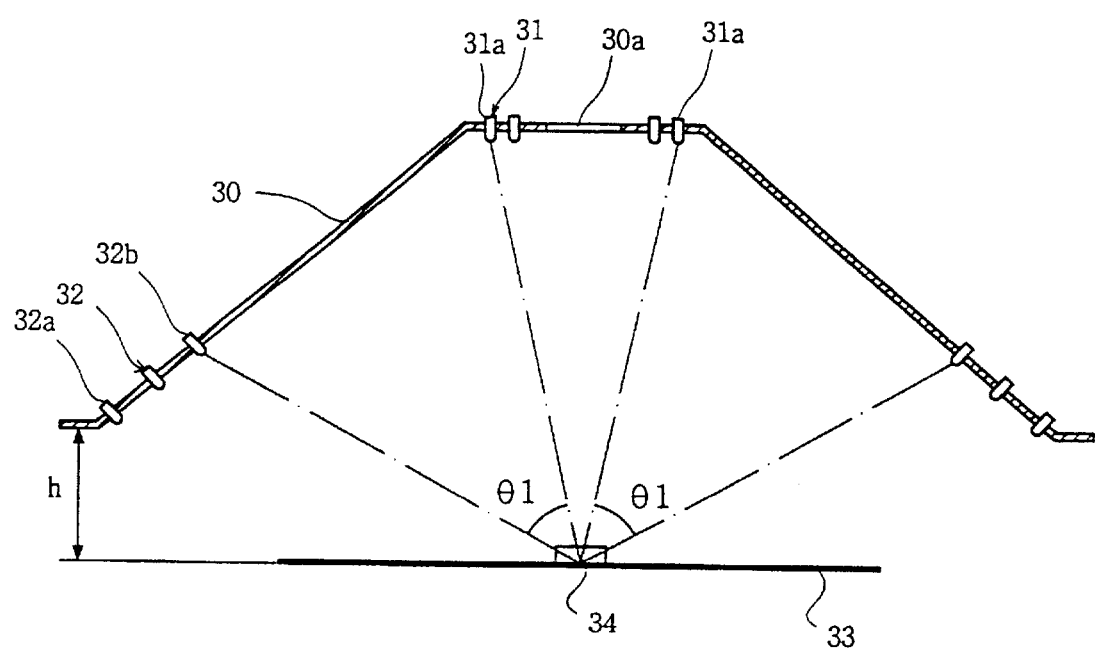
FIG. 4 illustrates a position to install second illuminating means of the illuminating and optical apparatus of FIG. 3, in accordance with the present invention.

The second illuminating means 32 includes a plurality of lamps formed in concentric circles and arranged in a plurality of ring-shaped fixtures having different diameters and heights. For example, the fixtures include 3 rows of ring-shaped fixtures to obtain an image, of which shade is inverted to that obtained by the first illuminating means 31 at the metal surfaces having the reflection characteristic of a mirror, such as the soldered surface of the inspecting part 34, an electrode surface, and the like. The ring-shaped lamps 32a disposed at the lowest end of the second illuminating means 32 are positioned close to the lower portion of the tilted plane of the second illuminating means 32 formed in the circular cone of the fixed member 30. A ring of a plurality of lamps 32b disposed at the highest end of the second illuminating means 32, as shown in FIG. 4, are located exactly at an angle $\theta_1$ of more than 30 degrees between a straight line formed by the ring shaped lamps 31a arranged at an outermost portion of the first illuminating means 31, connecting the center of the inspecting part 34 positioned at a standard height (h) and another straight line formed by the ring shaped lamps 32b, connecting the center of the inspecting part 34 positioned at the standard height (h).

Light emitting diodes are, for example, used by the first and second illumination means 31, 32.

At this time, the first illuminating means 31 is arranged in two rows of ring-shaped fixtures and the second illuminating means 32 is arranged in three rows of ring-shaped fixtures, both of which are described as an example. The first and second illuminating means 31, 32 can also be arranged in a plurality of ring-shaped fixtures, more than two and three rows of ring-shaped fixtures.

Reference numeral 40 denotes optical means fixed over the fixed member 30 to photograph the inspecting part 34.

The optical means 40 includes large and small view cameras 41, 42 to respectively obtain different view sizes of images in accordance with the sizes of the inspecting part 34, wherein the large and small view camera s 41, 42 respectively include large and small view lenses 41a, 42a (or a small magnitude lens 41a and large magnitude lens 42a) to collect the reflected light drawn through reflected light transmitting means 43, which will be described below.

The reflected light transmitting means 43 includes a half mirror 431 which transmits a half of the light reflected by the inspecting part 34 to continuously advance the half of the light to a proceeding direction and reflects the other half of the light to change a proceeding direction of the other half of the light to an angle of 90 degrees. A total reflection mirror 432 having a large view, reflects the light reflected by the half mirror 431 at the angle of 90 degrees to identically proceed to the axis of the large view camera 41 and the large view lens 41a. A first total reflection mirror 433 having a small view, changes the proceeding direction of the light transmitted through the half mirror 431 at the angle of 90 degrees. A second total reflection mirror 434 having a small view, reflects again the light, whose proceeding direction was changed at 90 degrees by the first total reflection mirror 433 of the small view, to identically advance the light to the axis of the small view camera 42 and the small view lens 42a.

For example, the half mirror 431 and the first total reflection light mirror 433 having the small view are made of triangular prisms, and the total reflection mirror 432 having the large view and the second total reflection mirror 434 having the small view are made of planar mirrors.

The illuminating and optical apparatus of the present invention thus constructed completely collects the light emitted by the first and second illuminating means 31, 32 including the plurality of lamps 31a, 32a arranged in a plurality of rows around a view axis 40a of the large and small view cameras 41, 42. The lamps 31a, 32a are arranged around the view axis 40a of the large and small view cameras 41 and 42 at an angle to draw sufficient light from the light emitting diodes and reflected by the inspecting part 34. The optical means 40 includes the large and small view cameras 41, 42 to respectively obtain different view sizes of images in accordance with the sizes of the inspecting part 34. The illuminating and optical apparatus of the present invention maximizes the uniformity of brightness within the range of the view.

Figure 5:
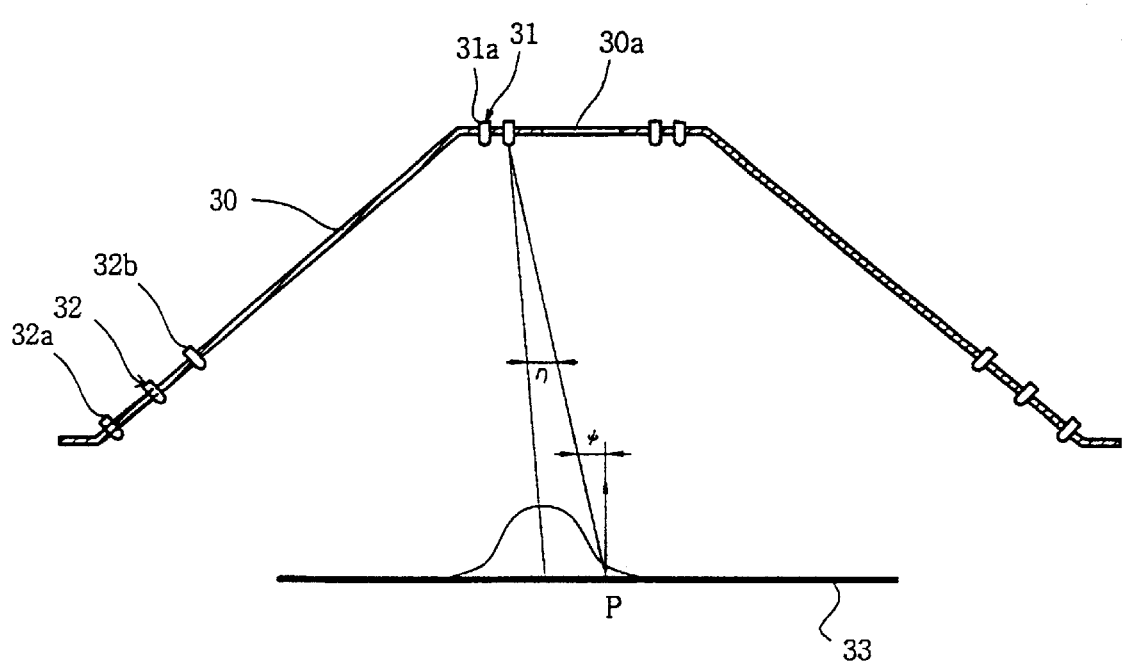
FIG. 5 illustrates distribution of emitted light in polar coordinates, provided that a lamp from first illuminating means is a light emitting source in the illuminating and optical apparatus of FIG. 3, in accordance with the present invention

FIG. 5 illustrates the distribution of emitted light in polar coordinates, provided that a lamp from the first illuminating means 31 is a light emitting source in the illuminating and optical apparatus, in accordance with the present invention.

In FIG. 5, the amount of light emitted by the lamp and a centering of a light axis of the lamp, can be explained using a shape of a Gaussian distribution in a mathematical formula as follows:

$$I(\eta) = \frac{\phi}{2\pi\sigma} \exp\left[\frac{n^2}{\sigma^2}\right] \qquad \text{Mathematical formula 1}$$

where η is a radian between the optical axis of the lamp and a predetermined light ray, I(η) is an intensity of the light of the lamp at an angle η relative to the optical axis of the lamp, φ is a power constant of the light emitted by the lamp, and a is a light dispersion angle of the lamp.

In FIG. 5, if a lamp illuminates a predetermined surface at the distance of I, the amount of the light E to be reflected along the view axis of the camera at a predetermined point P(x,y) of the surface is as follows:

$$E = I(\eta)\frac{\cos(\varphi)}{l^2} \; [\text{W/m}^2] \qquad \text{Mathematical formula 2}$$

where φ is an angle between a light ray and the view axis of the camera.

In addition, the total amount of the light emitted by a plurality of N lamps, drawn and reflected at a point P(x,y) can be estimated by adding the amount of light reflected by each lamp in mathematical formula 3 as follows:

$$E(x, y) = \sum_{i=0}^{N} Ei(x, y) \; [\text{W/m}^2] \qquad \text{Mathematical formula 3}$$

The angle of the optical axis of a lamp tilted from the view axis 40*a* of the large and small view cameras 41, 42 is determined when lamps are arranged to maximize the amount of reflecting light within view and, at the same time, to maximize the uniformity of reflecting light within the range of the view in the following mathematical formula 4:

$$C=\alpha\Sigma E(x,y)+\beta\cdot Q \qquad \text{Mathematical formula 4}$$

where α and β are weight values, E is a total quantity of light accumulated within the range of the view, and Q is a uniformity, that is, an inverse value of the brightness distribution within the range of the view.

Figure 6:
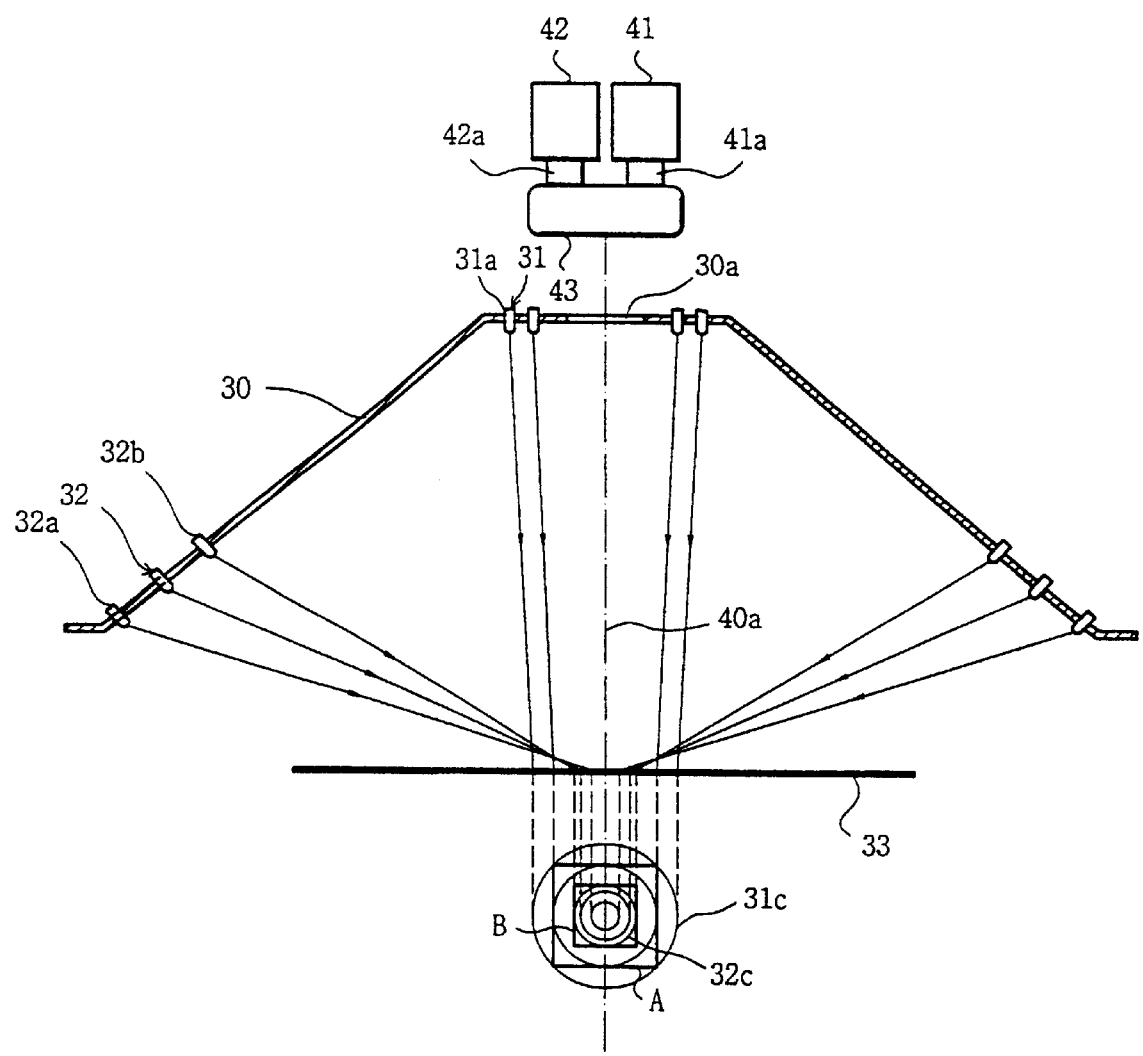
FIG. 6 illustrates angles of incident light drawn into the first and second illuminating means of the illuminating and optical apparatus of FIG. 3, in accordance with the present invention.

FIG. 6 illustrates angles of incident light from the first and second illuminating means 31, 32, which are arranged as described above.

As shown in FIG. 6, traces 31*c* of an intersection of the incident light from the first illuminating means 31 incident on the PCB 33 are shaped in a circle, and traces 32*c* of an intersection of the incident light of the second illuminating means 32 incident on the PCB 33 is shaped in a circle as well. The traces 31*c* and 32*c* are different in diameter from each other.

In addition, the second illuminating means 32 is arranged in a plurality of rows of ring-shaped fixtures to widen the angle of the light of the lower ring-shaped fixtures of lamps, thereby minimizing the light interference caused by other neighboring parts.

Under the aforementioned illumination, the reflected light radiated from the inspecting part 34 is divided into two by the half mirror 431 of the reflected light transmitting means 43. The first half of the reflected light divided into half is photographed by the large view camera 41 through the total reflection mirror 432 having a large view and the large view lens 41*a*. On the other hand, the other half of the reflected light is photographed by the small view camera 42 through the first and second total reflection mirror 433, 434 having a small view and the small view lens 42*a*.

Figure 7:
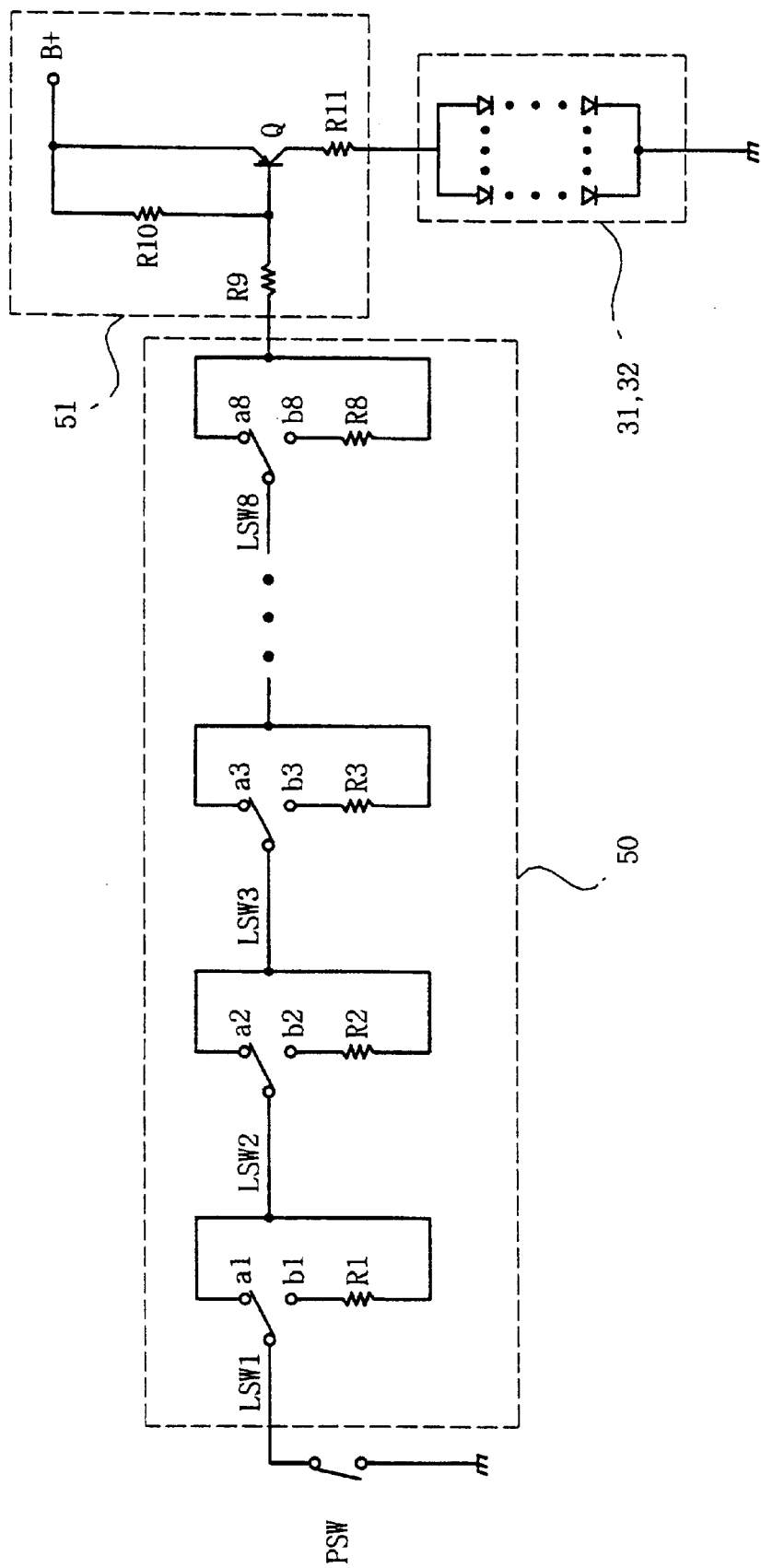
FIG. 7 illustrates a structure of control means which controls turning on/off and brightness of the first and second illuminating means of the illuminating and optical apparatus of FIG. 3, in accordance with the present invention.

FIG. 7 illustrates the structure of the control means which turns on/off the first and second illuminating means 31, 32 and controls the brightness of the illuminating and optical apparatus in accordance with the present invention.

As described above, resistors R1–R8 are respectively connected in series between one side of fixed elements a1–a8 and the other side of fixed elements b1–b8 of a plurality of light switches LSW1–LSW8. A connecting point of the one side of the fixed elements a1–a7 and the resistors R1–R7 of a plurality of light switches LSW1–LSW7 are respectively connected with operating elements of a plurality of light switches LSW2–LSW8, thereby forming a light control unit 50.

The operating elements of the light switch LSW1 are connected to ground by way of a power switch PSW. The connecting point of the one side of the fixed element a8 and the resistor R8 of the light switch LSW8 is connected through the resistor R9 to the resistor R10 and the base of the transistor (Q), so that a collector of the transistor (Q) is connected through the resistor R11 to the first illuminating means 31, thereby forming an output unit 51.

All of the resistors R–R8 are set up at different resistance values as follows: R1=2R2=4R3=8R4=16R5=32R6=64R7=128R8.

The control means, which controls the turning-on/off and brightness of the second illuminating means 32, is constructed in the same structure as the one which controls the turning-on/off and brightness of the first illuminating means 31.

In the control means of the present invention thus constructed, in the event that the power switch PSW is connected to turn on power and the operating elements of the light switches LSW1–LSW8 are connected to the one side of fixed elements a–a8, the voltage applied to the base of the transistor (Q) is low to increase the voltage difference between the emitter and the base of the transistor (Q). Thus, a large amount of electric current flows to the collector of the transistor (Q) to turn on the lamps of the first and second illuminating means 31, 32 very brightly to illuminate the inspecting part 34.

Furthermore, in the event that the operating elements of the light switches LSW1–LSW8 are connected to the other side of fixed elements b1–b8, the voltage applied to the base of the transistor (Q) is high enough to decrease the voltage difference between the emitter and the base of the transistor (Q). Thus, a small amount of electric current flows to the collector of the transistor (Q) to turn on the lamps of the first and second illuminating means 31, 32 less brightly to illuminate the inspecting part 34. At this time, the resistance values of resistors R1–R8 are differently set up as follows: R1=2R2=4R3=8R4=16R5=32R6=64R7=128R8. As operating elements of the light switches LSW1–LSW8 are selectively turned around, the lamps of the first and second illuminating means 31, 32 can be controlled at 256 levels of brightness to illuminate the inspecting part 34.

When the inspecting part 34 is inspected with the illuminating and optical apparatus of the present invention, the first illuminating means 31 is turned on at first to illuminate the part 34 with the second illuminating means 32 being turned off. At this time, the part 34 is photographed by the large and small view cameras 41, 42 to obtain a first image.

Then, the second illuminating means 32 is turned on to illuminate the part 34 with the first illuminating means 31 being turned off. At this time, the part 34 is photographed by the large and small view cameras 41, 42 to obtain a second image.

The two images obtained of which shade is inverted to a soldered unit and an electrode unit made of a metal surface of the inspecting part 34, are used for determining the mounted and soldered states thereof. In other words, as shown in FIG. 8, if the first illuminating means 31 is turned on to illuminate the inspecting part 34 with the second illuminating means 32 being turned off, a soldering fillet part formed at the tilted plane is shown as a negative area (dark area) due to a characteristic of light reflection while the ends of an electrode and a pad made in the horizontal plane are shown as a positive area (bright area).

Figure 8:
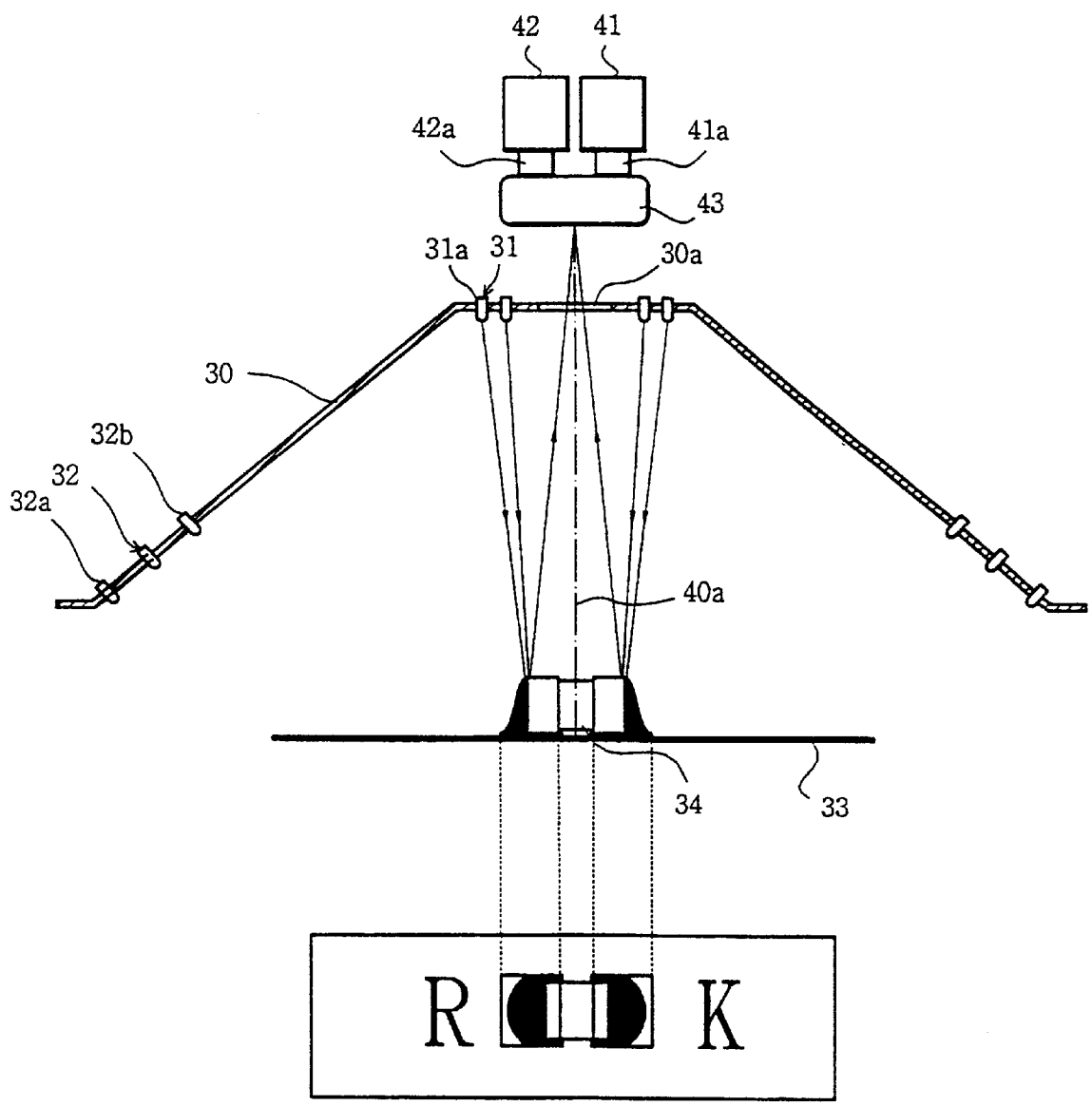
FIG. 8 illustrates pictures of image signals photographed in accordance with the first illuminating means turned on and the second illuminating means turned off of the illuminating and optical apparatus of FIG. 3, in accordance with the present invention.
Figure 9:
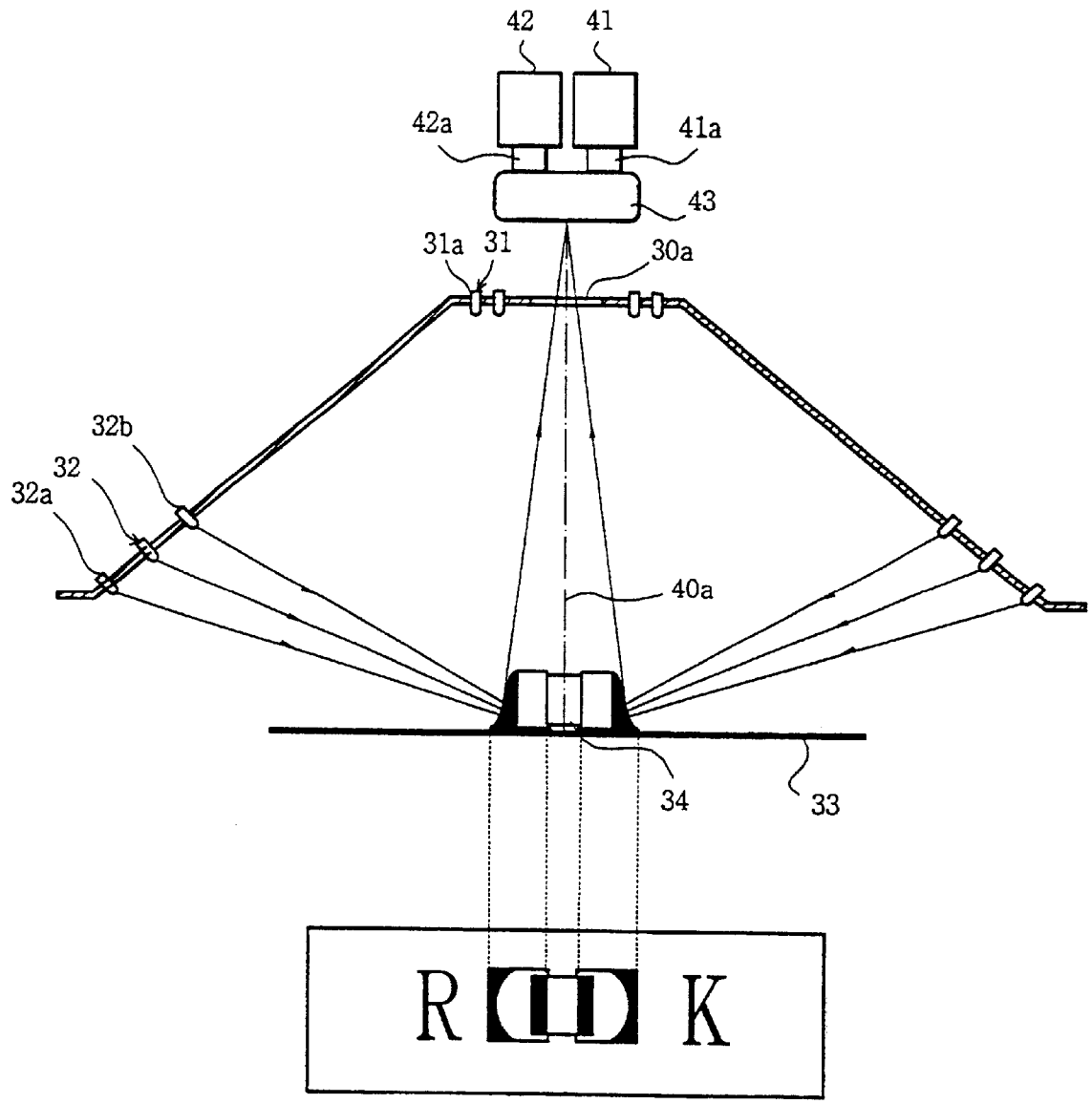
FIG. 9, illustrates pictures of image signals photographed in accordance with the first illuminating means turned off and the second illuminating means turned on of the illuminating and optical apparatus of FIG. 3, in accordance with the present invention.

As shown in FIG. 9, if the second illuminating means 32 is turned on to illuminate the inspecting part 34 with the first illuminating means 31 being turned off, the shade has been inverted, exactly opposite to the case shown in FIG. 8. Therefore, the soldering fillet part formed at the tilted plane is shown as the positive area while the ends of the electrode and the pad formed at the horizontal plane are shown as the negative area.

With the aforementioned two images obtained as such, the areas already designated for inspection are used for determining the mounted and soldered states of the inspecting part 34. For example, the two images can be separately used, or an image created by subtracting or adding the other image from or to one image can be also used for inspecting the mounted and soldered states of the inspecting part 34.

Industrial Application

As described above, there are advantages to the illuminating and optical apparatus of the present invention in that the apparatus can selectively control horizontal or vertical illumination and consistently set an illuminating brightness according to a digital method. Further, the illuminating and optical apparatus of the present invention can properly arrange the focus of incident light of the light emitting means larger than the view to improve the uniformity of illuminating brightness and to increase the inspecting speed and reliability by efficiently corresponding to the size of various parts. In addition, the illuminating and optical apparatus can maximize the quantity of light which is reflected from the inspecting part and incident into the camera and, at the same time, the illuminating angle of the illuminating means can be properly controlled to keep the distribution of the quantity of light even at its maximum.

What is claimed is:

1. An illuminating and optical apparatus for inspecting soldering of a PCB, comprising:
   a fixed member comprising a horizontal plane at an upper plane thereof and a tilted plane at the side thereof;
   first illuminating means disposed at the upper plane of the fixed member for illuminating an inspecting part attached to the PCB;
   second illuminating means disposed at the tilted plane of the fixed member for illuminating the inspecting part to obtain an image having a shade inverted to that obtained by the first illuminating means;
   first and second view cameras;
   control means for controlling a brightness of the first and second illuminating means and turning power thereof on/off; and
   optical means disposed at the upper plane of the fixed member for photographing large and small views of the inspecting part illuminated by the first and second illuminating means under the control of the control means, wherein the optical means comprises the first and second view cameras to draw light being reflected by the inspecting part and to obtain the large and small views, respectively, of the inspecting part.

2. The apparatus as recited in claim 1, further comprising a photograph hole formed on the fixed member, wherein the first illuminating means comprises lamps arranged in ring-shaped fixtures of different diameters therebetween and having identical heights thereto, and the lamps are installed adjacent to the photograph hole of the optical means formed on the fixed member.

3. The apparatus as recited in claim 1, wherein the second illuminating means comprises lamps arranged in ring-shaped fixtures of different diameters and heights therebetween.

4. The apparatus as recited in claim 3, wherein the lamps arranged in ring-shaped fixtures located at a lowest end of the second illuminating means are disposed adjacent to a lower portion of the tilted plane of the fixed member.

5. The apparatus as recited in claim 3, further comprising:
   lamps arranged in ring-shaped fixtures located at an uppermost portion of the second illuminating means and located at a predetermined angle between a straight line formed by the ring-shaped fixtures arranged at an outermost portion of the first illuminating means connecting a center of the inspecting part positioned at a predetermined height and another straight line formed by the ring-shaped fixtures arranged at the uppermost portion of the second illuminating means connecting the center of the inspecting part positioned at the predetermined height.

6. The apparatus as recited in claim 5, wherein the predetermined angle comprises an angle of at least 30 degrees.

7. The apparatus as recited in claim 1, wherein traces of an intersection of incident lights from the first and second illuminating means incident on the PCB are respectively shaped in circles, the traces being different in diameter from each other.

8. The apparatus as recited in claim 7, wherein the first illuminating means comprises lamps arranged in ring-shaped fixtures of different diameters therebetween and having identical heights thereto, wherein the lamps are installed adjacent to a photograph hole of the optical means formed on the fixed member.

9. The apparatus as recited in claim 7, wherein the second illuminating means comprises lamps arranged in ring-shaped fixtures of different diameters and heights therebetween.

10. The apparatus as recited in claim 9, wherein the lamps arranged in ring-shaped fixtures located at a lowest end of the second illuminating means are disposed adjacent to a lower portion of the tilted plane of the fixed member.

11. The apparatus as recited in claim 9, further comprising:
    lamps arranged in ring-shaped fixtures located at an uppermost portion of the second illuminating means and located at a predetermined angle between a straight line formed by the ring-shaped fixtures arranged at an outermost portion of the first illuminating means connecting a center of the inspecting part positioned at a predetermined height and another straight line formed by the ring-shaped fixtures arranged at the uppermost portion of the second illuminating means connecting the center of the inspecting part positioned at the predetermined height.

12. The apparatus as recited in claim 11, wherein the predetermined angle comprises an angle of more than 30 degrees.

13. The apparatus as recited in claim 1, wherein the control means comprises:

a power switch;

a light control unit varying a resistance value by controlling a plurality of light switches; and an output unit outputting electric current in accordance with the resistance value of the light control unit when the power switch is turned on and applying the electric current to the first and second illuminating means.

14. The apparatus as recited in claim 13, wherein the light control unit varies by predetermined levels of resistance by controlling the light switches.

15. The apparatus as recited in claim 14, wherein the predetermined levels of resistance comprise 256 levels.

16. The apparatus as recited in claim 1, wherein the optical means further comprises:

reflected light transmitting means for transmitting a half of the light reflected by the inspecting part, wherein the first and second view cameras comprise large and small view cameras, respectively, which respectively photograph the half of the light reflected by the inspecting part; and large and small view lenses respectively assembled in front of the large and small view cameras controlling view sizes of images to be photographed by the large and small view cameras.

17. The apparatus as defined in claim 13, wherein the reflected light transmitting means comprises a half mirror for transmitting a half of the light reflected by an inspected part to continuously advance to its proceeding direction and for reflecting the other half of the light to change its proceeding direction to an angle of 90 degrees; a total reflection mirror of large view for reflecting again the light reflected by the half mirror at the angle of 90 degrees to proceed in the direction of the axis of the large view camera; a first total reflection mirror of small view for changing the proceeding direction of the light transmitted through the half mirror at the angle of 90 a second total reflection mirror of small view for reflecting the light reflected by the first total reflection mirror of small view in the direction of the axis of the small view camera; large view and small view lenses for transmitting the light reflected by the total reflection mirror of large view and the second total reflection mirror into the large view camera and small view camera.

18. The apparatus as recited in claim 16, wherein the half mirror and the first total reflection mirror of the small view are triangular prisms, and the total reflection mirror of the large view and the second total reflection mirror of the small view are planar mirrors.

19. The apparatus as recited in claim 1 further comprising:

a camera; and optical axis control means for determining the optical axis of the first and second illuminating means to maximize a quantity of light which is reflected from the inspecting part and incident into the camera and to maximize a uniformity of reflecting light within a range of a view, the optical axis control means being operated in accordance with predetermined mathematical formulas.

20. The apparatus as recited in claim 19, wherein the mathematical formulas comprise:

$$I(\eta) = \frac{\phi}{2\pi\sigma} \exp\left[\frac{n^2}{\sigma^2}\right] \quad (1)$$

where η is a radian between the optical axis of the lamp and a predetermined light ray, I(η) is an intensity of the light of the lamp at an angle η relative to the optical axis of the lamp, φ is a power constant of the light emitted by the lamp, and σ is a light dispersion angle of the lamp;

$$E = I(\eta)\frac{\cos(\varphi)}{l^2} \quad [W/m^2] \quad (2)$$

where φ is an angle between a light ray and the view axis of the camera;

$$C = \alpha\Sigma E(x,y) + \beta \cdot Q \quad (3)$$

where α and β are weight values, E is a total quantity of light accumulated within the range of the view, and Q is an inverse value of the brightness distribution within the range of the view.

21. An illuminating and optical apparatus to inspect soldering of an inspecting part on a PCB, comprising:

large and small view cameras;

first and second illuminating units each comprising lamps arranged in rows around a view axis of the large and small view cameras at a predetermined angle, wherein the large and small view cameras draw sufficient light reflected by the inspecting part and obtain different view sizes of images in accordance with sizes of the inspecting part; and an illuminating and optical apparatus collecting light emitted by the first and second illuminating units.

22. An illuminating and optical apparatus for inspecting soldering of an inspecting part on a PCB, comprising:

light emitting parts to evenly illuminate the inspecting part; and a camera set comprising different view magnitudes to photograph different view sizes of images in accordance with the sizes of the inspecting part to inspect the mounted and soldered states of the inspecting part.

23. The apparatus as recited in claim 22, further comprising a fixed member comprising a horizontal plane at an upper plane thereof and a tilted plane at the side thereof;

a first illuminating unit disposed at the upper plane of the fixed member illuminating the inspecting part attached to the PCB;

a second illuminating unit disposed at the tilted plane of the fixed member illuminating the inspecting part to obtain an image having a shade inverted to that obtained by the first illuminating unit; and an optical unit disposed at the upper plane of the fixed member photographing large and small views of the inspecting part illuminated by the first and second illuminating units.

24. The apparatus as recited in claim 23, further comprising a photograph hole formed on the fixed member, wherein the first illuminating unit comprises lamps arranged in ring-shaped fixtures of different diameters therebetween and having identical heights thereto, and the lamps are installed adjacent to the photograph hole of the optical unit formed on the fixed member.

25. The apparatus as recited in claim 24, further comprising a photograph hole formed on the fixed member, wherein the second illuminating unit comprises lamps arranged in ring-shaped fixtures of different diameters and heights therebetween.

26. The apparatus as recited in claim 23, wherein traces of an intersection of incident lights from the first and second illuminating units incident on the PCB are respectively shaped in circles, the traces being different in diameter from each other.

27. The apparatus as recited in claim 22, further comprising:
- a first illuminating unit;
- a second illuminating unit; and
- lamps arranged in ring-shaped fixtures located at an uppermost portion of the second illuminating unit and located at a predetermined angle between a straight line formed by the ring-shaped fixtures arranged at an outermost portion of the first illuminating unit connecting a center of the inspecting part positioned at a predetermined height and another straight line formed by the ring-shaped fixtures arranged at the uppermost portion of the second illuminating unit connecting the center of the inspecting part positioned at the predetermined height.

28. The apparatus as recited in claim 22, wherein the light emitting parts comprise:
- a first illuminating unit illuminating the inspecting part attached to the PCB; and
- a second illuminating unit illuminating the inspecting part to obtain an image having a shade inverted to that obtained by the first illuminating unit.

29. The apparatus as recited in claim 22, further comprising a reflected light transmitter comprising:
- a half mirror to transmit a first half of the light reflected by the inspecting part to continuously advance the first half of the light to a proceeding direction and reflect a second half of the light reflected by the inspecting part to change a proceeding direction of the second half of the light to an angle of 90 degrees.

30. The apparatus as recited in claim 29, wherein the camera set comprises a large view camera and a small view camera and a large view lens and a small view lens in front of the large and small view cameras, respectively, to control the view sizes of the images to be photographed by the large and small view cameras.

31. The apparatus as recited in claim 30, further comprising:
- a total reflection mirror comprising a large view to reflect the light reflected by the half mirror at the angle of 90 to identically proceed to the axis of the large view camera and the large view lens.

32. The apparatus as recited in claim 31, further comprising:
- a first total reflection mirror comprising a small view to change a proceeding direction of the light transmitted through the half mirror at the angle of 90 degrees; and
- a second total reflection mirror comprising a small view to reflect again the light of which proceeding direction was changed at 90 degrees by the first total reflection mirror, and to identically advance the light to the axis of the small view camera and the small view lens.

* * * * *